(12) United States Patent
Li et al.

(10) Patent No.: US 6,465,509 B2
(45) Date of Patent: Oct. 15, 2002

(54) PYRONES AS INHIBITORS OF CYCLOOXYGENASE-2

(75) Inventors: Chun-Sing Li, Dollard des Ormeaux; Cheuk Kun Lau, Ile Bizard; Michel Therien, Laval, all of (CA); Petpiboon Prasit, Rancho Santa Fe, CA (US)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/892,941

(22) Filed: Jun. 27, 2001

(65) Prior Publication Data

US 2002/0058690 A1 May 16, 2002

Related U.S. Application Data

(60) Provisional application No. 60/215,694, filed on Jun. 30, 2000.

(51) Int. Cl.[7] .......................... A61K 31/35; A61K 31/44
(52) U.S. Cl. .................... 514/460; 514/459; 514/282.1; 549/292; 549/293; 549/294; 546/282.1
(58) Field of Search ................. 514/460, 459, 514/336; 546/282.1; 549/292, 293, 294

(56) References Cited

U.S. PATENT DOCUMENTS

| 5,474,995 A | 12/1995 | Ducharme et al. |
| 5,677,318 A | 10/1997 | Lau |
| 6,020,343 A | 2/2000 | Belley et al. |

FOREIGN PATENT DOCUMENTS

| WO | WO 94/26731 | 11/1994 |
| WO | WO 95/00501 | 1/1995 |
| WO | WO 95/18799 | 7/1995 |
| WO | WO 96/36623 | 11/1996 |
| WO | WO 98/41511 | 9/1998 |
| WO | WO 01/68633 | 9/2001 |

OTHER PUBLICATIONS

Chun–Sing Li, et a.; Bioorganic & Medicinal Chemistry Letter 9 (1999) 3181–3186.*
Y. Leblanc, et al.; Bioorganic & Medicinal Chemistry Letters 9 (1999) 2207–2212.*

* cited by examiner

*Primary Examiner*—Amelia Owens
(74) *Attorney, Agent, or Firm*—Baynard Yuro; David L. Rose

(57) ABSTRACT

The invention encompasses the novel compounds of Formula I, which are useful in the treatment of cyclooxygenase-2 mediated diseases.

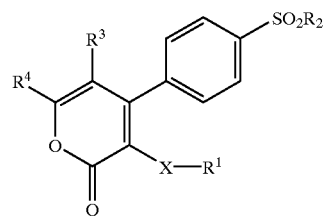

The invention also encompasses certain pharmaceutical compositions comprising compounds of Formula I as well as methods of treating cyclooxygenase-2 mediated diseases comprising administering to a patient in need of such treatment a non-toxic therapeutically effective amount of a compound of Formula I.

18 Claims, No Drawings

PYRONES AS INHIBITORS OF CYCLOOXYGENASE-2

CROSS-REFERENCE TO RELATED APPLICATION

This application claims the benefits of U.S. Provisional Application No. 60/215,694, filed on Jun. 30, 2000.

BACKGROUND OF THE INVENTION

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of cyclooxygenase-2 inhibitors is given in an article by John Vane, *Nature*, Vol. 367, pp. 215–216, 1994, and in an article in *Drug News and Perspectives*, Vol. 7, pp. 501–512, 1994.

SUMMARY OF THE INVENTION

The invention encompasses the novel compounds of Formula I, which are useful in the treatment of cyclooxygenase-2 mediated diseases:

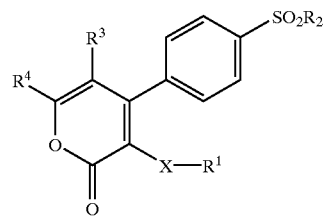

or a pharmaceutically acceptable salt thereof wherein:
X is selected from the group consisting of:
  (a) a bond,
  (b) —$(CH_2)_m$—, wherein m=1 or 2,
  (c) —C(O)—,
  (d) —O—,
  (e) —S—, and
  (f) —$N(R^5)$—;
$R^1$ is selected from the group consisting of:
  (a) $C_{1-10}$alkyl, optionally substituted with 1–3 substituents independently selected from the group consisting of:
    (1) hydroxy,
    (2) halo,
    (3) $C_{1-10}$alkoxy,
    (4) $C_{1-10}$alkylthio, and
    (5) CN,
  (b) phenyl or naphthyl, and
  (c) heteroaryl, which is comprised of a monocyclic aromatic ring of 5 atoms having one hetero atom which is S, O or N, and optionally 1, 2, or 3 additional N atoms; or
  a monocyclic ring of 6 atoms having one hetero atom which is N, and optionally 1, 2, or 3 additional N atoms,
  wherein groups (b) and (c) above are each optionally substituted with 1–3 substituents independently selected from the group consisting of:
    (1) halo,
    (2) $C_{1-10}$alkoxy,
    (3) $C_{1-10}$alkylthio,
    (4) CN,
    (5) $C_{1-10}$alkyl, optionally substituted to its maximum with halo, and
    (6) $N_3$;
$R^2$ is selected from the group consisting of
  (a) $C_{1-6}$alkyl, optionally substituted to its maximum with halo,
  (b) $NH_2$, and
  (c) $NHC(O)C_{1-10}$alkyl, optionally substituted to its maximum with halo;
$R^3$ and $R^4$ are each independently selected from the group consisting of:
  (a) hydrogen,
  (b) halo, and
  (c) $C_{1-6}$alkyl, optionally substituted to its maximum with halo; and
$R^5$ is selected from the group consisting of:
  (a) hydrogen and
  (b) $C_{1-6}$alkyl, optionally substituted to its maximum with halo.

The invention also encompasses certain pharmaceutical compositions comprising compounds of Formula I as well as methods of treating cyclooxygenase-2 mediated diseases comprising administering to a patient in need of such treatment a non-toxic therapeutically effective amount of a compound of Formula I.

DETAILED DESCRIPTION OF THE INVENTION

The invention encompasses the novel compounds of Formula I, which are useful in the treatment of cyclooxygenase-2 mediated diseases

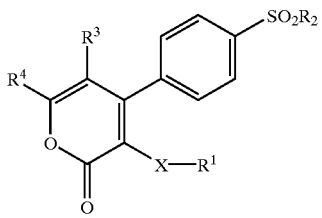

I or a pharmaceutically acceptable salt thereof wherein:
X is selected from the group consisting of:
(a) a bond,
(b) —(CH$_2$)$_m$—, wherein m=1 or 2,
(c) —C(O)—,
(d) —O—,
(e) —S—, and
(f) —N(R$^5$)—;
R$^1$ is selected from the group consisting of:
(a) C$_{1-10}$alkyl, optionally substituted with 1–3 substituents independently selected from the group consisting of:
(1) hydroxy,
(2) halo,
(3) C$_{1-10}$alkoxy,
(4) C$_{1-10}$alkylthio, and
(5) CN,
(b) phenyl or naphthyl, and
(c) heteroaryl, which is comprised of a monocyclic aromatic ring of 5 atoms having one hetero atom which is S, O or N, and optionally 1, 2, or 3 additional N atoms; or
a monocyclic ring of 6 atoms having one hetero atom which is N, and optionally 1, 2, or 3 additional N atoms,
wherein groups (b) and (c) above are each optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and
(6) N$_3$;
R$^2$ is selected from the group consisting of
(a) C$_{1-6}$alkyl, optionally substituted to its maximum with halo,
(b) NH$_2$, and
(c) NHC(O)C$_{1-10}$alkyl, optionally substituted to its maximum with halo;
R$^3$ and R$^4$ are each independently selected from the group consisting of:
(a) hydrogen,
(b) halo, and
(c) C$_{1-6}$alkyl, optionally substituted to its maximum with halo; and
R$^5$ is selected from the group consisting of:
(a) hydrogen and
(b) C$_{1-6}$alkyl, optionally substituted to its maximum with halo.

An embodiment of the invention is that wherein X is a bond.

Another embodiment of the invention is that wherein X is —O—.

Another embodiment of the invention is that wherein X is —S—.

Another embodiment of the invention is that wherein R$^2$ is CH$_3$.

Another embodiment of the invention is that wherein R$^3$ is hydrogen.

Another embodiment of the invention is that wherein m is 1.

Another embodiment of the invention encompasses compounds of Formula I wherein R$^1$ is phenyl, optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and
(6) N$_3$.

A class of this embodiment encompasses compounds wherein R$^1$ is as defined above and R$^2$ is CH$_3$. Another class of this embodiment encompasses compounds wherein R$^1$ is as defined above and R$^3$ is H.

Another embodiment of the invention encompasses compounds of Formula I wherein R$^1$ is heteroaryl, which is comprised of a monocyclic aromatic ring of 5 atoms having one hetero atom which is S, O or N, and optionally 1, 2, or 3 additional N atoms; or a monocyclic ring of 6 atoms having one hetero atom which is N, and optionally 1, 2, or 3 additional N atoms, wherein heteroaryl is optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and
(6) N$_3$.

Another embodiment of the invention encompasses compounds of Formula I wherein R$^1$ is pyridyl, optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and
(6) N$_3$.

Another embodiment of the invention encompasses compounds of Formula I wherein R$^1$ is C$_{1-6}$alkyl, optionally substituted with hydroxy.

In another aspect, the invention encompasses a pharmaceutical composition comprising a compound of Formula I in combination with a pharmaceutically acceptable carrier.

In another aspect, the invention encompasses a method of treating or preventing an inflammatory disease in a mammalian patient in need of such treatment or prevention comprising administering to said patient a compound of Formula I in an amount effective to treat or prevent said inflammatory disease.

In another aspect, the invention encompasses a method of treating or preventing a cyclooxygenase-2 mediated disease advantageously treated by an active agent that selectively inhibits cyclooxygenase-2 in preference to cyclooxygenase-1 in a mammalian patient in need of such treatment or prevention comprising administering to said patient a compound of Formula I in an amount effective to treat or prevent said cyclooxygenase-2 mediated disease.

In another aspect, the invention encompasses the use of a compound of Formula I in the manufacture of a medicament for the treatment of an inflammatory disease susceptible to treatment with a non-steroidal anti-inflammatory agent.

The invention is illustrated by the compounds of the Examples disclosed herein as well as the compounds of Table I.

For purposes of this specification, the following abbreviations have the indicated meanings:

| | |
|---|---|
| AA | = arachidonic acid |
| Ac = | acetyl |
| AIBN = | 2,2'-azobisisobutyronitrile |
| Bn = | benzyl |
| CHO = | chinese hamster ovary |
| CMC = | 1-cyclohexyl-3-(2-morpholinoethyl) carbodiimidemetho-p-toluenesulfonate |
| COX = | cyclooxygenase |
| DBU = | diazabicyclo[5.4.0]undec-7-ene |
| DMAP = | 4-(dimethylamino)pyridine |
| DMF = | N,N-dimethylformamide |
| DMSO = | dimethyl sulfoxide |
| $Et_3N$ = | triethylamine |
| HBSS = | Hanks balanced salt solution |
| HEPES = | N-[2-Hydroxyethyl]piperazine-$N^1$-[2-ethanesulfonic acid] |
| HWB = | human whole blood |
| IPA = | isopropyl alcohol |
| KHMDS = | potassium hexamethyldisilazane |
| LDA = | lithium diisopropylamide |
| LPS = | lipopolysaccharide |
| mCPBA = | metachloro perbenzoic acid |
| MMPP = | magnesium monoperoxyphthalate |
| Ms = | methanesulfonyl = mesyl |
| MsO = | methanesulfonate = mesylate |
| NBS = | N-bromosuccinimide |
| NCS = | N-chlorosuccinimide |
| NIS = | N-iodosuccinimide |
| NSAID = | non-steroidal anti-inflammatory drug |
| ODCB = | o-dichlorobenzene |
| Oxone ® = | potassium peroxymonosulfate |
| PCC = | pyridinium chlorochromate |
| PDC = | pyridinium dichromate |
| r.t. = | room temperature |
| rac. = | racemic |
| Tf = | trifluoromethanesulfonyl = triflyl |
| TFAA = | trifluoroacetic anhydride |
| TfO = | trifluoromethanesulfonate = triflate |
| THF = | tetrahydrofuran |
| TLC = | thin layer chromatography |
| TMPD = | N,N,N',N'-tetramethyl-p-phenylenediamine |
| Ts = | p-toluenesulfonyl = tosyl |
| TsO = | p-toluenesulfonate = tosylate |
| Tz = | 1H (or 2H)-tetrazol-5-yl |

-continued

| | |
|---|---|
| $SO_2Me$ = | methyl sulfone (also $SO_2CH_3$) |
| $SO_2NH_2$ = | sulfonamide |

| Alkyl group abbreviations | Dose Abbreviations |
|---|---|
| Me = methyl | bid = bis in die = twice daily |
| Et = ethyl | qid = quater in die = four times a day |
| n-Pr = normal propyl | id = ter in die = three times a day |
| i-Pr = isopropyl | |
| n-Bu = normal butyl | |
| i-Bu = isobutyl | |
| s-Bu = secondary butyl | |
| t-Bu = tertiary butyl | |
| c-Pr = cyclopropyl | |
| c-Bu = cyclobutyl | |
| c-Pen = cyclopentyl | |
| c-Hex = cyclohexyl | |

For purposes of this specification, "alkyl" means linear branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl- 4-propylnonyl, cyclopropyl, cyclopentyl, cycloheptyl, adamantyl, cyclododecylmethyl, 2-ethyl-1-bicyclo[4.4.0]decyl and the like.

For purposes of this specification, "alkoxy" means alkoxy groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like.

For purposes of this specification, "alkylthio" means alkylthio groups of the indicated number of carbon atoms of a straight, branched or cyclic configuration. Examples of alkylthio groups include methylthio, propylthio, isopropylthio, cycloheptylthio, etc. By way of illustration, the propylthio group signifies —$SCH_2CH_2CH_3$.

For purposes of this specification "halo" means F, Cl, Br, or I.

Exemplifying the invention are the following compounds:

(1) 4-(4-Methylsulfonyl)phenyl-3-phenyl-pyran-2-one, (2) 3-(4-Fluorophenyl)-6-methyl-4-(4-methylsulfonyl) phenyl-pyran-2-one, (3) 3-(3-Fluorophenyl)-6-methyl-4-(4-methylsulfonyl) phenyl-pyran-2-one, (4) 6-Methyl-4-(4-methylsulfonyl)phenyl-3-phenyl-pyran-2-one, (5) 6-Difluoromethyl-4-(4-methylsulfonyl)phenyl-3-phenyl-pyran-2-one, (6) 6-Fluoromethyl-4-(4-methylsulfonyl)phenyl-3-phenyl-pyran-2-one, (7) 6-Methyl-4-(4-methylsulfonyl)phenyl-3-phenylthio-pyran-2-one, (8) 6-Methyl-4-(4-methylsulfonyl)phenyl-3-phenoxy-pyran-2-one, (9) 6-Methyl-4-(4-methylsulfonyl)phenyl-3-pyridin-3-yl-pyran-2-one,

(10) 3-Isopropylthio-6-methyl-4-(4-methylsulfonyl) phenyl-pyran-2-one,

(11) 4-(4-Methylsulfonyl)phenyl)-3-phenylthio-6-trifluoromethyl-pyran-2-one,

(12) 3-Isopropylthio-4-(4-methylsulfonyl)phenyl-6-trifluoromethyl-pyran-2-one,

(13) 4-(4-Methylsulfonyl)phenyl-3-phenyl-6-(2,2,2-trifluoroethyl)-pyran-2-one, and

(14) 3-(3-Hydroxy-3-methylbutyl)-6-methyl-4-(4-methylsulfonyl)phenyl-pyran-2-one.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment that follows, references to the compounds of Formula I are meant to also include the pharmaceutically acceptable salts.

The compounds of Formula I are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. The compounds of Formula I may also be of use in the treatment and/or prevention of cyclooxygenase-mediated proliferative disorders such as may occur in diabetic retinopathy and tumour angiogenesis.

The compounds of Formula I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis) and for the treatment of glaucoma.

By virtue of its high cyclooxygenase-2 (COX-2) activity and/or its specificity for cyclooxygenase-2 over cyclooxygenase-1 (COX-1), The compounds of Formula I are useful as alternatives to conventional non-steroidal anti-inflammatory drugs (NSAID'S), particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; and those prior to surgery or taking anticoagulants.

Similarly, the compounds of Formula I are useful as a partial or complete substitute for conventional NSAIDs in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of a compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases, the compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compounds of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods:

Method A

An appropriately 3-substituted 5-hydroxy-4-(4-methylsulfonyl)phenyl-5H-furan-2-one II (WO 9636623) is reacted with a ylide, generated from the reaction of (methoxymethyl)triphenylphosphonium chloride with a base such as potassium t-butoxide in a solvent such as THF to give a penta-2,4-dienoic acid intermediate III. Subsequently refluxing in a solvent such as toluene with an acidic catalyst such as p-toluenesulfonic acid affords pyrone IV.

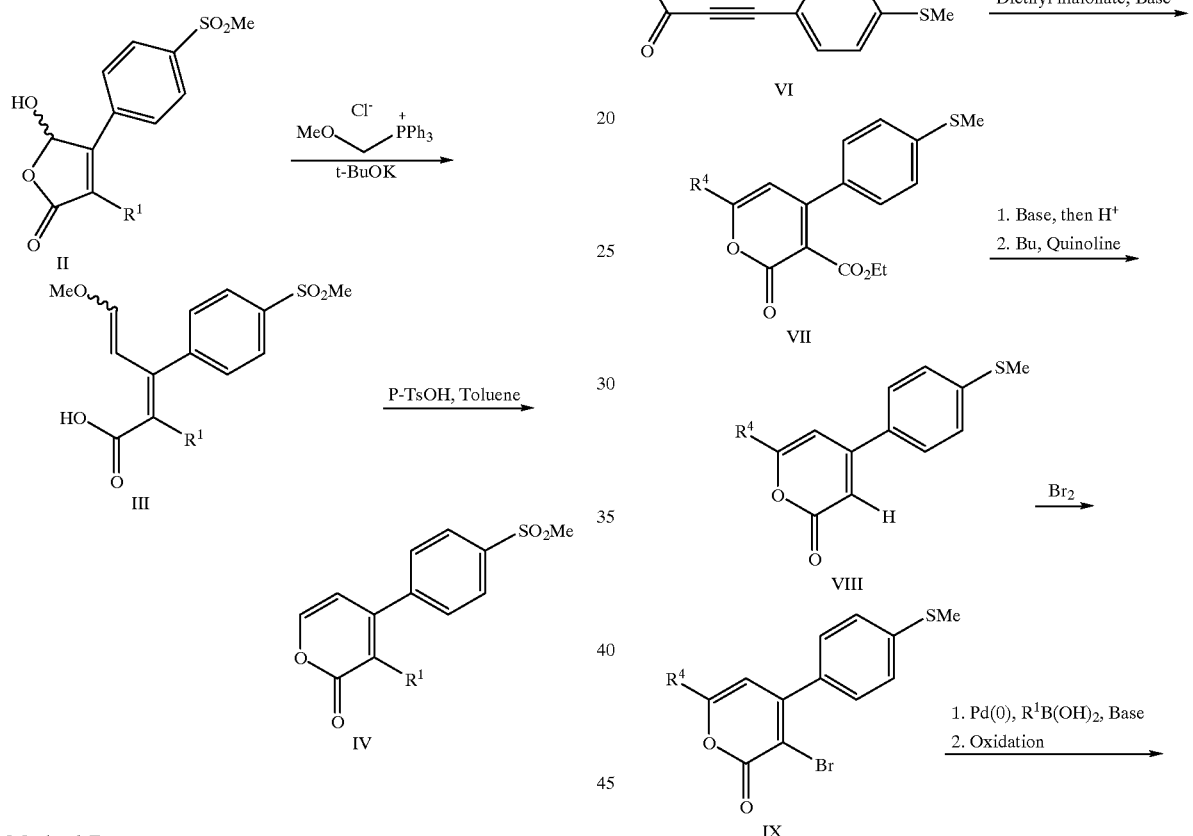

Method B

4-Bromthioanisole is reacted with an alk-1-yn-3-ol in the presence of a palladium (0) catalyst, catalytic amount of a copper (1) salt such as CuI, catalytic amount of triphenylphosphine and a base such as triethylamine in a solvent such as CH$_3$CN to give the alkyn-ol intermediate V. Oxidation with an oxidant such as MnO$_2$ provides ketone VI, which is reacted with diethyl malonate in the presence of a base such as activated barium hydroxide in an alcoholic solvent such as ethanol to give the pyrone intermediate VII. Hydrolysis of the ester with a base such as aqueous sodium hydroxide and followed by decarboxylation with copper bronze in quinoline affords intermediate VIII. Bromination of VIII in a solvent such as CH$_2$Cl$_2$ gives IX. Coulping with IX with an appropriately boronic acid in the presence of a palladium (0) catalyst and a base such as sodium carbonate, and subsequently oxidation with an oxidant such as mCPBA affords pyrone X.

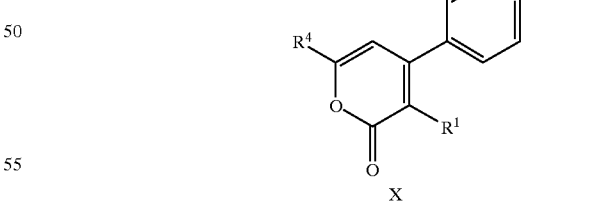

Method C

Sufide IX is oxidized with an oxidant such as mCPBA to give sulfone XI, which is subsequently reacted with an appropriate nucleophile in the presence of an alkaline base such as NaOH or in the presence of an alkaline base such as K$_2$CO$_3$ with CuO to give pyrone I.

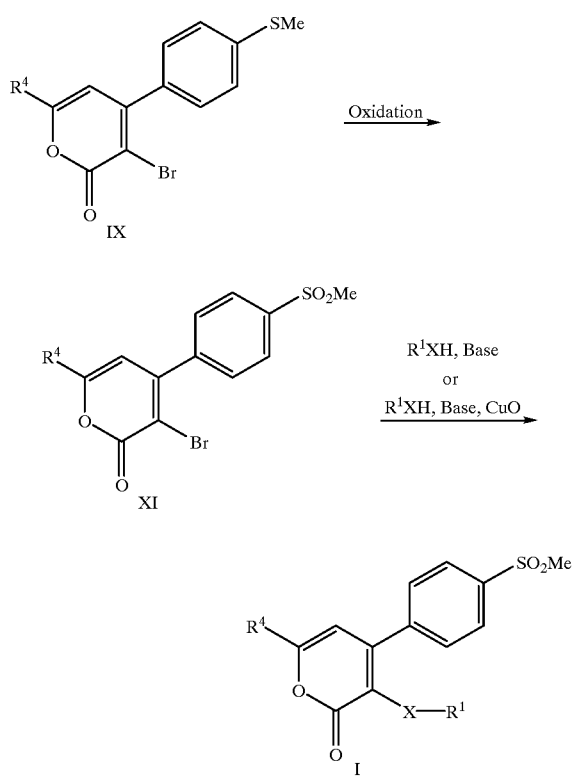

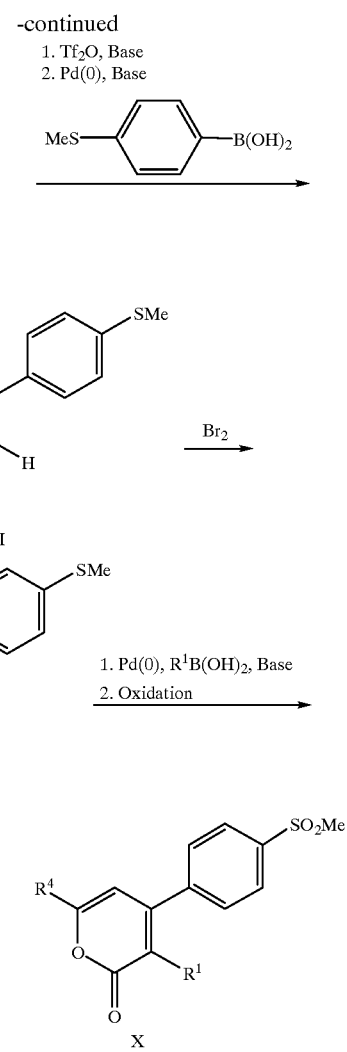

Method D tert-Butyl acetoacetate is treated with sodium hydride followed by n-butyllithium and the resulting dianion is reacted with an ester to provide a diketo ester intermeidate XII. Treatment with trifluoroacetic acid gives an acid intermediate, which is stirred with acetic anhydride to furnish an acetylated pyran-2-one intermediate. Subsequent hydrolysis with an aqueous alkaline base such as sodium hydroxide affords the hydroxyl pyran-2-one intermediate XII. Reaction with trifluoromethanesulfonic anhydride yields a triflate intermediate, which is coupled with 4-(methylthio)phenylboronic acid in the presence of a Pd (0) catalyst and a base such as sodium carbonate gives intermediate VIII. This intermediate VIII is then further converted to pyrone X as described in Method B.

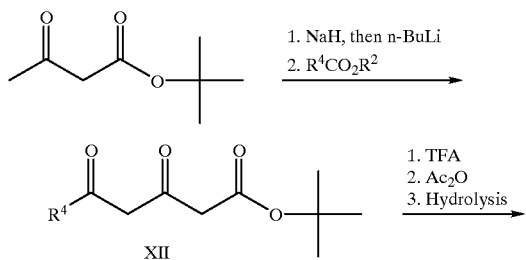

Method E

Pyrone XIV, obtained from pyrone intermediate IX with an appropriate coupling reaction such as Suzuki reaction as described in Method D, is oxidized with selenium dioxide to give an aldehyde intermediate XV. Treatment with diethylaminosulfur trifluoride followed by oxidation with an oxidant such as mCPBA affords pyrone XVI.

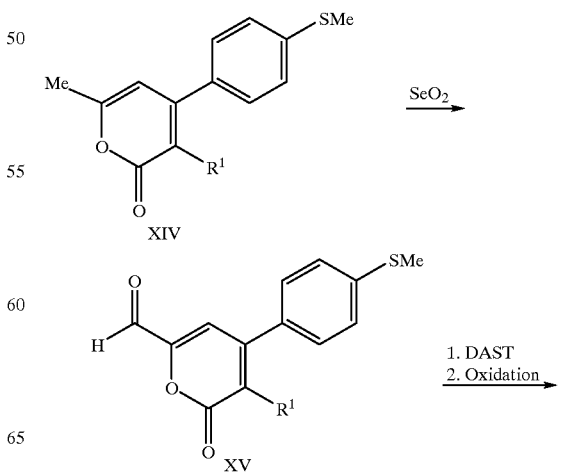

-continued

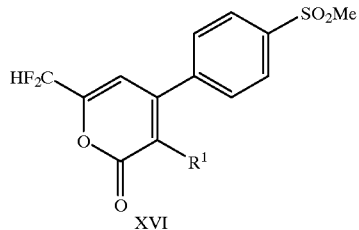

XVI

-continued

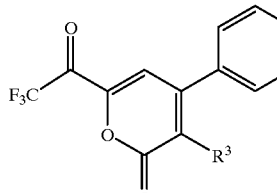

XIX

PhOCSCl/DMAP →

Method F

Pyrone XV obtained from Method E is reduced with a reducing agent such as sodium borohydride to give alcohol XVII. Treatment with diethylaminosulfur trifluoride followed by oxidation with an oxidant such as mCPBA affords pyrone XVIII.

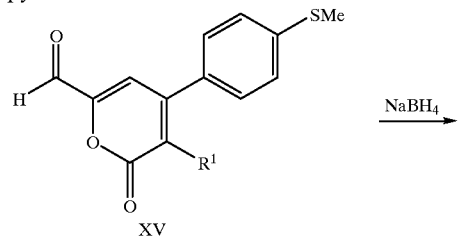

XV

NaBH₄ →

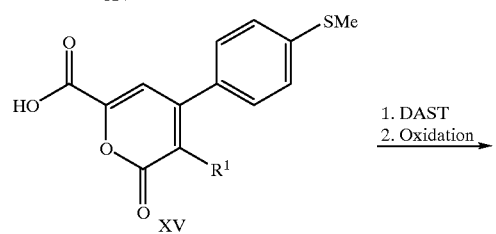

XV

1. DAST
2. Oxidation →

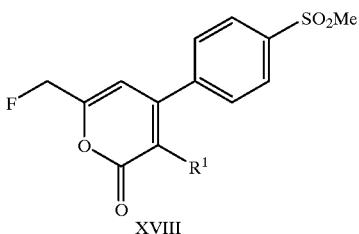

XVIII

Method G trimethyl(trifluoromethyl)silane in the presence of a fluoride ion such as tetrabutylammonium fluoride to give the trifluoromethanol intermediate XIX. Treatment with phenyl chlorothionoformate in the presence of DMAP in a solvent such as acetonitrile affords thiocarbonate intermediate XX. Radical deoxygenation with tributyltin hydride generated in situ from tributyltin chloride with sodium borohydride yields XXI. Subsequent oxidation with an oxidant such as mCPBA gives the desired pyrone XXII.

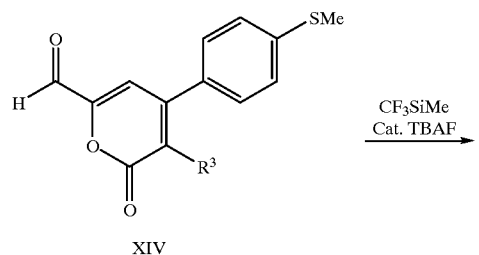

XIV

CF₃SiMe
Cat. TBAF →

Bu₃SnCl
NaBH₄/AlBN →

XX

Oxidation →

XXI

XXII

Method H

Pyrone IX obtained from Method B is coupled with 2-methyl-3-butyn-2-ol in the presence of Cu (I) and Pd (II) catalysts to provide the intermediate XXIII. Pyrone XXIII is then oxidized with an oxidant such as MMPP and followed by hydrogenation to give the desired pyrone XXV.

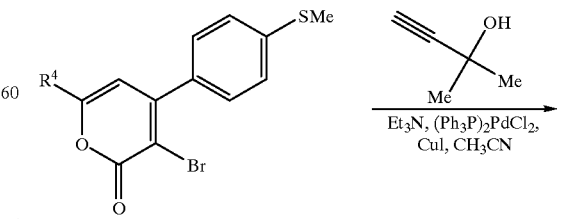

IX

Et₃N, (Ph₃P)₂PdCl₂,
CuI, CH₃CN →

-continued
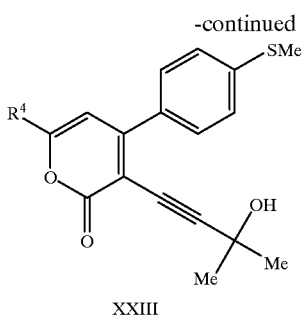
XXIII
Oxidation →
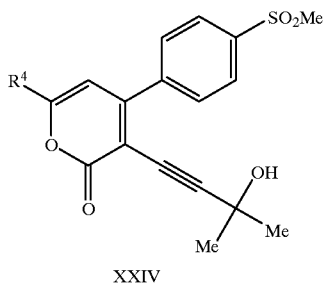
XXIV
Reduction →
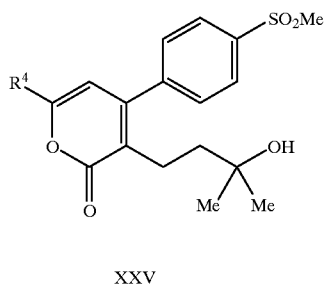
XXV
Representative Compounds
Tables I illustrates novel compounds of the present invention.
TABLE I
| Example | Method |
|---|---|
| 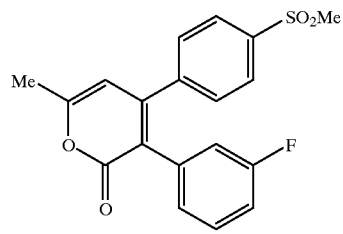 | 1 | A |
| 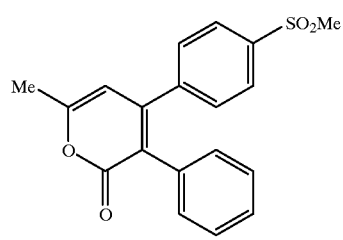 | 2 | B |
TABLE I-continued
| Example | Method |
|---|---|
| 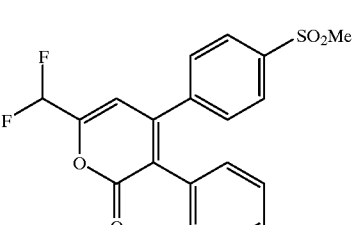 | 3 | B |
| 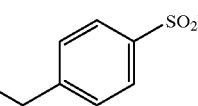 | 4 | B |
|  | 5 | E |
| 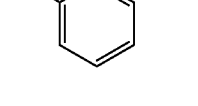 | 6 | F |
|  | 7 | C |
| 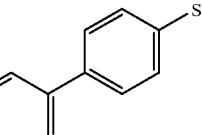 | 8 | C |

TABLE I-continued

| | Example | Method |
|---|---|---|
| [structure: 6-Me, 4-(4-SO2Me-phenyl), 3-(3-pyridyl)-pyran-2-one] | 9 | B |
| [structure: 6-Me, 4-(4-SO2Me-phenyl), 3-(S-CH(Me)2)-pyran-2-one] | 10 | C |
| [structure: 6-CF3, 4-(4-SO2Me-phenyl), 3-(S-phenyl)-pyran-2-one] | 11 | D |
| [structure: 6-CF3, 4-(4-SO2Me-phenyl), 3-(S-CH(Me)2)-pyran-2-one] | 12 | D |
| [structure: 6-CH2CF3, 4-(4-SO2Me-phenyl), 3-phenyl-pyran-2-one] | 13 | G |
| [structure: 6-Me, 4-(4-SO2Me-phenyl), 3-(CH2CH2C(Me)2OH)-pyran-2-one] | 14 | H |

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (?) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), M.P. (melting point), L (liter(s)), mL (milliliters), g (gram (s)), mg (milligrams(s)), mol (moles), mmol (millimoles), eq (equivalent(s)).

EXAMPLE 1

4-(4-Methylsulfonyl)phenyl-3-phenyl-pyran-2-one

Step 1: 5-Methoxy-3-(4-methylsulfonyl)phenyl-2-phenyl-penta-2,4-dienoic acid

To a suspension of (methoxymethyl)triphenylphosphonium chloride (13 g, 38 mmol) in THF (80 mL) was added a solution of 1M t-BuOK (40 mL) in THF. The mixture was stirred at r.t. for 30 min. A solution of 5-hydroxy-4-(4-methylsulfonyl)phenyl-3-phenyl-5H-furan-2-one (WO 9636623) (4.0 g, 12.1 mmol) in THF was added. The mixture was then stirred at r.t. for 1.5 h., quenched with $H_2O$, acidified with HOAc and extracted with EtOAc. The EtOAc extract was washed with 1M aqueous NaOH (2×). The combined alkaline washings were washed with EtOAc (1×), acidified with 6M aqueous HCl and extracted with EtOAc. The EtOAc extract was washed with $H_2O$, dried (anhydrous $MgSO_4$) and concentrated. The residue was swished with $Et_2O$ to give 3.5 g (81%) of the title compound.

Step 2: 4-(4-Methylsulfonyl)phenyl-3-phenyl-pyran-2-one

To a suspension of 5-methoxy-3-(4-methylsulfonyl)phenyl-2-phenyl-penta-2,4-dienoic acid (190 mg, 0.53 mmol) and p-TsOH (50 mg, 0.3 mmol) in toluene (15 mL) was refluxed for 6 h. Solvent was then evaporated in vacuo. Chromatography over silica gel and elution with hexanes:EtOAc (1:2) gave 110 mg of title compound as a white foam.

$^1$H NMR (Acetone-$d_6$) δ 7.84 (d, 2H), 7.80 (d, 1H), 7.47 (d, 2H), 7.25–7.10 (m, 5H), 6.57 (d, 1H), 3.09 (s, 3H).

EXAMPLE 2

3-(4-Fluorophenyl)-6-methyl-4-(4-methylsulfonyl)phenyl-pyran-2-one

Step 1: 4-(4-Methylthio)phenyl-3-butyn-2-ol

A mixture of 4-bromothioanisole (46 g, 0.2 mol), 3-butyn-2-ol (17.8 g, 0.25 mol), $Et_3N$ (58 g, 0.57 mol), triphenylphosphine (600 mg, 2.3 mmol), CuI (400 mg, 2.1 mmol) and Pd(PPh$_3$)$_4$ (800 mg, 0.7 mmol) in CH$_3$CN (300 mL) was heated at 60° C. for 3 days and 80° C. for 1 day. The mixture was then evaporated in vacuo. The residue was then diluted with H$_2$O and extracted with EtOAc. The EtOAc extract was washed with H$_2$O (2×), dried (anhydrous MgSO$_4$) and concentrated. Chromatography over silica gel and elution with hexanes with 5% EtOAc removed the unreacted 4-bromothioanisole and followed by hexanes:EtOAc (3:1) provided 28.5 g (74%) of the title compound as a green-yellow oil.

$^1$H NMR (Acetone-d$_6$) δ 7.32 (d, 2H), 7.25 (d, 2H), 4.68 (q, 1H), 4.36 (d, 1H), 2.50 (s, 3H), 1.44 (d, 3H).

Step 2: 4-(4-Methylthio)phenyl-3-butyn-2-one

To a solution of 4-(4-methylthio)phenyl-3-butyn-2-ol (28 g, 0.15 mol) in THF (800 mL) was added activated MnO$_2$ (65 g, 0.74 mol). After stirring for 30 min at r.t., more MnO$_2$ (30 g, 0.35 mol) was added. The mixture was then stirred for another 1 h. and filtered through celite. The filter cake was washed with EtOAc. The combined filtrates were concentrated and chromatographed over silica gel eluting with hexanes:EtOAc (5:1) to give 23 g (83%) of the title compound as a yellow oil.

$^1$H NMR (Acetone-d$_6$) δ 7.55 (d, 2H), 7.34 (d, 2H), 2.56 (s, 3H), 2.38 (s, 3H).

Step 3: 6-Methyl-4-(4-methylthio)phenyl-2-oxo-2H-pyran-3-carboxylic acid ethyl ester A mixture of 4-(4-methylthio)phenyl-3-butyn-2-one (5.0 g, 26 mmol), diethyl malonate (21 g, 0.13 mol) and activated barium hydroxide (1.5 g, 8.9 mmol) in EtOH (500 mL) was heated at 90° C. for 2 days. After cooling to r.t., the mixture was filtered through celite. Solvent was removed in vacuo. The residue was partitioned between EtOAc-H$_2$O. The organic layer was separated, washed with diluted aqueous HCl, H$_2$O; dried (anhydrous MgSO$_4$) and concentrated. Chromatogarphy over silica gel and elution with hexanes-EtOAc (2.5:1) provided 2.9 g (36%) of the title compound as a yellow solid.

$^1$H NMR (Acetone-d$_6$) δ 7.45-7.30 (m, 4H), 6.38 (s, 1H), 4.15 (q, 2H), 2.55 (s, 3H), 2.32 (s, 3H), 1.14 (t, 3H).

Step 4: 6-Methyl-4-(4-methylthio)phenyl-2-oxo-2H-pyran-3-carboxylic acid

A mixture of 6-methyl-4-(4-methylthio)phenyl-2-oxo-2H-pyran-3-carboxylic acid ethyl ester (5.5 g, 18.1 mmol) and 1M aqueous NaOH (20 mL, 20 mmol) in THF-EtOH (1:1, 120 mL) was stirred at r.t. for 1 h and then heated at 90° C. for 1 h. After cooling to r.t., the mixture was diluted with H$_2$O, acidified with 6M aqueous HCl and extracted with EtOAc. The EtOAc extract was washed with 1M aqueous NaOH (2×), brine; dried (anhydrous MgSO$_4$), concentrated and swished with Et$_2$O to give 450 mg of 6-methyl-4-(4-methylthio)phenyl-pyran-2-one. The alkaline washings were combined, washed with EtOAc, acidified with 6M aqueous HCl and extracted with EtOAc. The EtOAc extract was washed with brine, dried (anhydrous MgSO$_4$) and concentrated to give 3.5 g (70%) the title compound as a brown foam.

$^1$H NMR (Acetone-d$_6$) δ 7.46 (d, 2H), 7.35 (d, 2H), 6.40 (s, 1H), 2.56 (s, 3H), 2.35 (s, 3H).

Step 5: 6-Methyl-4-(4-methylthio)phenyl-pyran-2-one

A mixture of 6-methyl-4-(4-methylthio)phenyl-2-oxo--2H-pyran-3-carboxylic acid (3.5 g, 12.7 mmol) and copper bronze (1 g, 15.7 mmol) in quinoline (50 mL) was heated at 180–190° C. for 30 min. After cooling to r.t., the mixture was partitioned between H$_2$O and EtOAc. The EtOAc extract was washed with diluted aqueous HCl (3×), brine; dried (anhydrous MgSO$_4$) and concentrated. Chromatography over silica gel and elution with hexanes:EtOAc (2:1) gave 1.5 g (51%) of title compound as dark brown powders after swishing with Et$_2$O.

$^1$H NMR (Acetone-d$_6$) δ 7.70 (d, 2H), 7.38 (d, 2H), 6.57 (s, 1H), 6.33 (s, 1H), 2.55 (s, 3H), 2.28 (s, 3H).

Step 6: 3-Bromo-6-methyl-4-(4-methylthio)phenyl-pyran-2-one

To a solution of 6-methyl-4-(4-methylthio)phenyl-pyran-2-one (1.2 g, 5.2 mmol) and HOAc (1 mL) in CH$_2$Cl$_2$ (50 mL) at r.t. was added a solution of 1M Br$_2$ in CH$_2$Cl$_2$ (5.5 mL, 5.5 mmol). The mixture was stirred at r.t. for 30 min. and more Br$_2$ solution (5 mL, 5 mmol) was added. The mixture was then diluted with H$_2$O, washed with aqueous Na$_2$S$_2$O$_3$ solution, brine; dried (anhydrous MgSO$_4$) and concentrated. Chromatography over silica gel and elution with hexanes:EtOAc (2:1) and swishing with Et$_2$O gave 1.3 g (80%) of title compound as a pale yellow solid.

$^1$H NMR (Acetone-d$_6$) δ 7.47 (d, 2H), 7.38 (d, 2H), 6.27 (s, 1H), 2.55 (s, 3H), 2.27 (s, 3H).

Step 7: 3-(4-Fluorophenyl)-6-methyl-4-(4-methylthio) phenyl-pyran-2-one

A mixture of 3-bromo-6-methyl-4-(4-methylsulfonyl) phenyl-pyran-2-one (300 mg, 0.96 mmol), 4-fluorophenylboronic acid (270 mg, 1.9 mmol), [1,1'-bis (diphenylphosphino)-ferrocene]dichloropalladium (II), dichloromethane complex (50 mg, 0.06 mmol) and 2M aqueous Na$_2$CO$_3$ (1.5 mL, 3 mmol) in DMF (8 mL) was heated at 80° C. for 2 h. After cooling to r.t., the mixture was diluted with H$_2$O and extracted with EtOAc. The EtOAc extract was washed with H$_2$O, dried (anhydrous MgSO$_4$) and concentrated. Chromatography over silica gel and elution with hexanes:EtOAc (3:1) yielded 280 mg (89%) of title compound as a yellow foam.

$^1$H NMR (Acetone-d$_6$) δ 7.20-6.90 (m, 8H), 6.33 (s, 1H), 2.46 (s, 3H), 2.31 (s, 3H).

Step 8: 3-(4-Fluorophenyl)-6-methyl-4-(4-methylsulfonyl) phenyl-pyran-2-one

To a solution of 3-(4-fluorophenyl)-6-methyl-4-(4-methylthio)phenyl-pyran-2-one (240 mg, 0.74 mmol) in CH$_2$Cl$_2$ (10 mL) at 0° C. was added mCPBA (57–86%, 400 mg). The mixture was slowly warmed to r.t. and stirred for 1 h. After dilution with more CH$_2$Cl$_2$, the mixture was washed 1M aqueous NaOH (2×), brine, dried (anhydrous MgSO$_4$) and concentrated. Chromatography over silica gel, elution with hexanes:EtOAc (1:3) and swishing with Et$_2$O gave 205 mg (77%) of title compound as a white powders.

$^1$H NMR (Acetone-d$_6$) δ 7.85 (d, 2H), 7.45 (d, 2H), 7.18 (m, 2H), 6.98 (m, 2H), 6.37 (s, 1H), 3.09 (s, 3H), 2.34 (s, 3H).

EXAMPLE 3

3-(3-Fluorophenyl)-6-methyl-4-(4-methylsulfonyl) phenyl-pyran-2-one

Step 1: 3-(3-Fluorophenyl)-6-methyl-4-(4-methylthio) phenyl-pyran-2-one

Following the procedure described for example 2, step 7; the title compound was prepared from 3-bromo-6-methyl-4-(4-methylthio)phenyl-pyran-2-one and 3-fluorophenylboronic acid.

$^1$H NMR (Acetone-d$_6$) δ 7.30 (m, 8H), 6.34 (s, 1H), 2.46 (s, 3H), 2.32 (s, 3H).

Step 2: 3-(3-Fluorophenyl)-6-methyl-4-(4-methylsulfonyl) phenyl-pyran-2-one

Following the procedure described for example 2, step 8; the title compound was prepared from the oxidation of 3-(3-fluorophenyl)-6-methyl-4-(4-methylthio)phenyl-pyran-2-one.

$^1$H NMR (Acetone-d$_6$) δ 7.86 (d, 2H), 7.48 (d, 2H), 7.25 (m, 1H), 7.05-6.85 (m, 3H), 6.38 (s, 1H), 3.09 (s, 3H), 2.35 (s, 3H).

EXAMPLE 4

6-Methyl-4-(4-methylsulfonyl)phenyl-3-phenyl-pyran-2-one

Step 1: 6-Methyl-4-(4-methylthio)phenyl-3-phenyl-pyran-2-one

Following the procedure described for example 2, step 7; the title compound was prepared from 3-bromo-6-methyl-4-(4-methylthio)phenyl-pyran-2-one and phenylboronic acid.

$^1$H NMR (Acetone-d$_6$) δ 7.25-7.05 (m, 9H), 6.32 (s, 1H), 2.45 (s, 3H), 2.31 (s, 3H).

Step 2: 6-Methyl-4-(4-methylsulfonyl)phenyl-3-phenyl-pyran-2-one

Following the procedure described for example 2, step 8; the title compound was prepared from the oxidation of 6-methyl-4-(4-methylthio)phenyl-3-phenyl-pyran-2-one.

$^1$H NMR (Acetone-d$_6$) δ 7.82 (d, 2H), 7.44 (d, 2H), 7.25-7.10 (m, 5H), 6.36 (s, 1H), 3.08 (s, 3H), 2.34 (s, 3H).

EXAMPLE 5

6-Difluoromethyl-4-(4-methylsulfonyl)phenyl-3-phenyl-pyran-2-one

Step 1: 4-(4-Methylthio)phenyl-6-oxo-5-phenyl-6H-pyran-2-carbaldehyde

A mixture of 6-methyl-4-(4-methylthio)phenyl-3-phenyl-pyran-2-one, from example 4, step 1, (1.0 g, 3.2 mmol) and selenium dioxide (1.0 g, 9.0 mmol) in 1,2-dichlorobenzene (3 mL) was heated at 160° C. for 1 h. After cooling to r.t., the mixture was chromatographed over silica gel and eluted with hexanes:EtOAc (3:2) to give 800 mg of yellow foam. The foam was swished with Et$_2$O to yield 600 mg (58%) of title compound as a yellow solid.

$^1$H NMR (Acetone-d$_6$) δ 9.62 (s, 1H), 7.41 (s, 1H), 7.35-7.10 (m, 9H), 2.47 (s, 3H).

Step 2: 6-Difluoromethyl-4-(4-methylsulfonyl)phenyl-3-phenyl-pyran-2-one

To 4-(4-methylthio)phenyl-6-oxo-5-phenyl-6H-pyran-2-carbaldehyde (170 mg, 0.53 mmol) at r.t. was added diethylaminosulfur trifluoride (0.7 mL, 5.3 mmol). The mixture was heated at 65° C. for 15 min. and added dropwise carefully to ice-water. The whole mixture was extracted with EtOAc to give the 6-difluoromethyl-4-(4-methylthio)phenyl-3-phenyl-pyran-2-one intermediate as a pale yellow solid.

The above solid was oxidized in the usual manner as described for example 2, step 8 to give 125 mg (63%) of title compound as a pale yellow solid.

$^1$H NMR (Acetone-d$_6$) δ 7.86 (d, 2H), 7.51 (d, 2H), 7.25 (m, 5H), 6.95 (s, 1H), 6.77 (t, 1H), 3.10 (s, 3H).

EXAMPLE 6

6-Fluoromethyl-4-(4-methylsulfonyl)phenyl-3-phenyl-pyran-2-one

Step 1: 6-Hydroxymethyl-4-(4-methylsulfonyl)phenyl-3-phenyl-pyran-2-one

To 4-(4-methylthio)phenyl-6-oxo-5-phenyl-6H-pyran-2-carbaldehyde, from example 5, step 1, (680 mg, 2.1 mmol) in MeOH (100 mL) at r.t. was added NaBH$_4$ (100 mg, 12.5 mmol). The mixture was stirred for 30 min. and quenched with HOAc (300 μL). Solvent was removed in vacuo. The residue was diluted with H$_2$O and extracted EtOAc to give 680 mg of title compound as pale yellow powders.

$^1$H NMR (Acetone-d$_6$) δ 7.30-7.05 (m, 9H), 6.50 (s, 1H), 4.75 (t, 1H), 4.45 (d, 2H), 2.46 (s, 3H).

Step 2: 6-Fluoromethyl-4-(4-methylsulfonyl)phenyl-3-phenyl-pyran-2-one

To a solution of 6-hydroxymethyl-4-(4-methylsulfonyl)phenyl-3-phenyl-pyran-2-one (250 mg, 0.77 mmol) in CH$_2$Cl$_2$ (5 mL) at r.t. was added dropwise diethylaminosulfur trifluoride (250 μL, 1.9 mmol). The mixture was stirred for 15 min., then quenched with ice-water, and filtered through celite. The CH$_2$Cl$_2$ layer was separated, washed with brine, dried (anhydrous MgSO$_4$) and concentrated. Chromatography over silica gel and elution with hexanes:EtOAc (2:1) yielded 105 mg of 6-fluoromethyl-4-(4-methylsulfonyl)phenyl-3-phenyl-pyran-2-one as a yellow foam (~75% pure).

The above residue was oxidized in the usual manner as described for example 2, step 8 to give 65 mg of title compound (~75% pure).

$^1$H NMR (Acetone-d$_6$) δ 7.85 (d, 2H), 7.48 (d, 2H), 7.28-7.15 (m, 5H), 6.74 (m, 1H), 5.29 (d, 2H), 3.09 (s, 3H).

EXAMPLE 7

6-Methyl-4-(4-(methylsulfonyl)phenyl)-3-phenylthio-pyran-2-one

Step 1: 3-Bromo-6-methyl-4-(4-methylsulfonyl)phenyl-pyran-2-one

To a solution of 3-bromo-6-methyl-4-(4-methylthio)phenyl-pyran-2-one (2.5 g, 8.0 mmol) in CH$_2$Cl$_2$ (100 mL) at 0° C. was added mCPBA (57–86%, 6.0 g). The mixture was slowly warmed to r.t. and stirred for 1 h. After dilution with more CH$_2$Cl$_2$, the mixture was washed 1M aqueous NaOH (2×), brine, dried (anhydrous MgSO$_4$) and concentrated. The residue was swished with Et$_2$O containing a small amount of EtOAc to give 2.7 g of title compound as a pale yellow solid.

$^1$H NMR (Acetone-d$_6$) δ 8.09 (d, 2H), 7.76 (d, 2H), 6.31 (s, 1H), 3.20 (s, 3H), 2.30 (s, 3H).

Step 2: 6-Methyl-4-(4-(methylsulfonyl)phenyl)-3-phenylthio-pyran-2-one

To a solution of 3-bromo-6-methyl-4-(4-methylsulfonyl)phenyl-pyran-2-one (650 mg, 1.9 mmol) and thiophenol (230 mg, 2.1 mmol) in DMF (10 mL) at r.t. was added 10M aqueous NaOH (0.23 mL, 2.3 mmol). The mixture was stirred at r.t. for 2 h., then diluted with H$_2$O and extracted with EtOAc. The EtOAc extract was washed with H$_2$O and concentrated. Chromatography over silica gel and elution with hexanes:EtOAc (2:3) gave a yellow solid. Recrystallization from EtOH yielded 450 mg (64%) of title compound, contaminated with ~3% of 3-bromo-6-methyl-4-(4-methylsulfonyl)phenyl-pyran-2-one.

$^1$H NMR (Acetone-d$_6$) δ 8.00 (d, 2H), 7.69 (d, 2H), 7.28-7.10 (m, 5H), 6.39 (s, 1H), 3.16 (s, 3H), 2.34 (s, 3H).

EXAMPLE 8

6-Methyl-4-(4-(methylsulfonyl)phenyl)-3-phenoxy-pyran-2-one

A mixture of 3-bromo-6-methyl-4-(4-methylsulfonyl)phenyl-pyran-2-one, from example 7, step 1; (300 mg, 0.87 mmol), phenol (100 mg, 1.1 mmol), powdered anhydrous K$_2$CO$_3$ (240 mg, 1.7 mmol) and CuO (180 mg, 2.3 mmol) in pyridine (2 mL) was refluxed for 14 h. After cooling to r.t., the mixture was diluted with H$_2$O and extracted with EtOAc. The EtOAc layer was separated, washed with 1M aqueous HCl, brine, and concentrated. Chromatography over silica gel and elution with hexanes:EtOAc (1:2) yielded 10 mg of title compound (~95% pure) as a foam.

¹H NMR (Acetone-d₆) δ 7.99 (d, 2H), 7.85 (d, 2H), 7.27 (m, 2H), 7.05-6.90 (m, 3H), 6.45 (s, 1H), 3.13 (s, 3H), 2.34 (s, 3H).

Further elution also provided the debromonated product, 6-methyl-4-(4-methylsulfonyl)phenyl-pyran-2-one.

EXAMPLE 9

6-Methyl-4-(methylsulfonyl)phenyl)-3-pyridin-3-yl-pyran-2-one

Step 1: 6-Methyl-4-(methylthio)phenyl)-3-pyridin-3-yl-pyran-2-one

Following the procedure described for example 2, step 7; the title compound was prepared from 3-bromo-6-methyl-4-(4-methylthio)phenyl-pyran-2-one and pyridin-3-yl boronic acid.

¹H NMR (Acetone-d₆) δ 8.38 (m, 1H), 8.28 (m, 1H), 7.60 (m, 1H), 7.25 (m, 1H), 7.14 (m, 4H), 6.37 (s, 1H), 2.46 (s, 3H), 2.33 (s, 3H).

Step 2: 6-Methyl-4-(methylsulfonyl)phenyl)-3-pyridin-3-yl-pyran-2-one

Following the procedure described for example 2, step 8; the title compound was prepared from the oxidation of 6-methyl-4-(methylthio)phenyl)-3-pyridin-3-yl-pyran-2-one ¹H NMR (Acetone-d₆) δ 8.39 (m, 1H), 8.29 (m, 1H), 7.87 (d, 2H), 7.61 (m, 1H), 7.49 (d, 2H), 7.25 (m, 1H), 6.41 (s, 1H), 3.10 (s, 3H), 2.36 (s, 3H).

EXAMPLE 10

3-Isopropylthio-6-methyl-4-(4-(methylsulfonyl)phenyl)-pyran-2-one

Following the procedure described for example 7, step 2; the title compound was prepared from the coupling of 3-bromo-6-methyl-4-(4-methylsulfonyl)phenyl-pyran-2-one and 2-propanethiol.

¹H NMR (Acetone-d₆) δ 8.04 (d, 2H), 7.65 (d, 2H), 6.27 (s, 1H), 3.76 (m, 1H), 3.19 (s, 3H), 2.30 (s, 3H), 1.08 (d, 6H).

EXAMPLE 11

4-(4-(Methylsulfonyl)phenyl)-3-phenylthio-6-trifluoromethyl-pyran-2-one

Step 1: 6,6,6-Trifluoro-3,5-dioxo-hexanoic acid tert-butyl ester

To a suspension of 60% NaH (2.2 g, 55 mmol; washed with hexanes) in THF (250 mL) at 0° C. was added dropwise tert-butyl acetoacetate (8.0 g, 50.6 mmol) over a period of 15 min. The mixture was stirred for 15 min. and a homogenous solution solution resulted. A solution of 2.5M n-BuLi in hexanes (20.5 mL, 51 mmol) was added dropwise. After stirring for 15 min., 2,2,2-trifluoroethyl trifluoroacetate (11 g, 56 mmol) was added and the mixture was stirred for 30 min., quenched with HOAc, diluted with H₂O and extracted with EtOAc. The EtOAc extract was washed with H₂O, dried (anhydrous MgSO₄) and concentrated. Chromatography over silica gel and elution with hexanes:EtOAc (10:1), then hexanes:EtOAc (4:1) provided 5 g of title compound as a red-brown oil.

Step 2: 4-Hydroxy-6-trifluoromethyl-pyran-2-one

To a solution of 6,6,6-trifluoro-3,5-dioxo-hexanoic acid tert-butyl ester (5.0 g, 19.7 mmol) in CH₂Cl₂ (80 mL) was added trifluoroacetic acid (20 mL). The mixture was stirred for 1 h and then concentrated to give the crude acid intermediate. The residue was dissolved in acetic anhydride (20 mL), stirred at r.t. for 2 days and then concentrated to give an acetylated pyran-2-one intermediate. The crude residue was dissolved in MeOH (100 mL) and hydrolysed with 1M aqueous NaOH (20 mL). After stirring at r.t. for 30 min., the mixture was acidified with 6M aqueous HCl. Solvents were evaporated. The residue was diluted with H₂O and extracted with EtOAc. The EtOAc extract was concentrated to give 3 g of the title compound as pale yellow powders.

¹H NMR (DMSO-d₆) δ 9.52 (s, 1H), 6.96 (s, 1H), 5.74 (s, 1H).

Step 3: 4-(4-Methylthio)phenyl-6-trifluoromethyl-pyran-2-one

To a suspension of 4-hydroxy-6-trifluoromethyl-pyran-2-one (3.0 g, 16.7 mmol) in CH₂Cl₂ (80 mL) was added 2,6-lutidine (2.5 mL). The mixture was cooled to −78° C. and trifluoromethanesulfonic anhydride (3.0 mL, 17.8 mmol) was added dropwise over 15 min. The mixture was slowly warmed to 0° C. and quenched with H₂O. The CH₂Cl₂ layer was separated, washed with 1M aqueous HCl (2×), brine and concentrated. Chromatography over silica gel and elution with hexanes:EtOAc (6:1) gave 3.0 g of triflate intermediate as an oil.

A mixture of above triflate intermediate, 4-(methylthio)phenylboronic acid (1.6 g, 9.5 mmol), 2M aqueous Na₂CO₃ (9 mL, 18 mmol) and tetrakis(triphenylphosphine)palladium (0) (100 mg, 0.09 mmol) in THF (30 mL) was heated at 80–85° C. for 2 h. After cooling to r.t., the mixture was partitioned between EtOAc-H₂O. The EtOAc layer was washed with 1M aqueous NaOH (2×), 1M aqueous HCl, brine and concentrated. Chromatography over silica gel and elution with hexanes:EtOAc (3:1) gave 1.0 g of title compound as a light brown solid.

¹H NMR (Acetone-d₆) δ 7.86 (d, 2H), 7.42 (d, 2H), 7.39 (s, 1H), 6.82 (s, 1H), 2.57 (s, 3H).

Step 4: 3-Bromo-4-(4-methylthio)phenyl-6-trifluoromethyl-pyran-2-one

To a solution of 4-(4-methylthio)phenyl-6-trifluoromethyl-pyran-2-one (3.0 g, 10.5 mmol) in CHCl₃ (120 mL) was added Br₂ (1.5 ml, 29 mmol) at r.t. The mixture was heated at 70–75° C. for 16 h. After cooling to r.t., the mixture was washed with aqueous Na₂S₂O₃ (2×), brine, dried (anhydrous MgSO₄) and concentrated. Chromatography over silica gel and elution with hexanes:EtOAc (6:1) afforded 2.2 g of title compound as pale yellow solid.

¹H NMR (Acetone-d₆) δ 7.58 (d, 2H), 7.42 (d, 2H), 7.07 (s, 1H), 2.57 (s, 3H).

Step 5: 3-Bromo-4-(4-methylsulfonylphenyl-6-trifluoromethyl-pyran-2-one

To a solution of 3-bromo-4-(4-methylthio)phenyl-6-trifluoromethyl-pyran-2-one (1.1 g, 3.0 mmol) in CH₂Cl₂ (50 mL) at 0° C. was added mCPBA (57–86%, 1.7 g). The mixture was slowly warmed to r.t. and stirred for 1 h. After dilution with more CH₂Cl₂, the mixture was washed 1M aqueous NaOH (2×), brine, dried (anhydrous MgSO₄) and concentrated. The residue was swished with Et₂O to give 0.8 g of title compound as a white powder.

¹H NMR (Acetone-d₆) δ 8.15 (m, 4H), 7.46 (s, 1H), 6.98 (s, 1H), 3.20 (s, 3H).

Step 6: 4-(4-(Methylsulfonyl)phenyl)-3-phenylthio-6-trifluoromethyl-pyran-2-one

A mixture of 3-bromo-4-(4-methylsulfonylphenyl-6-trifluoromethyl-pyran-2-one (350 mg, 0.88 mmol), thiophenol (110 mL, 1.0 mmol) and 10M aqueous NaOH (105 mL, 1.1 mmol) in DMF (5 mL) was stirred at r.t. for 30 min., then diluted with H₂O, extracted with EtOAc. The EtOAc extract was washed with diluted aqueous NaOH (2×), brine and concentrated. Chromatography over silica gel and elution with hexanes:EtOAc (3:2) gave 130 mg of yellow foam. The residue was swished with Et$_2$O to give 110 mg of the title compound as a pale yellow solid.

$^1$H NMR (Acetone-d$_6$) δ 8.00 (d, 2H), 7.78 (d, 2H), 7.24 (m, 5H), 7.15 (s, 1H), 3.16 (s, 3H).

EXAMPLE 12

3-Isopropylthio-4-(4-(methylsulfonyl)phenyl)-6-trifluoromethyl-pyran-2-one

Following the procedure described for example 11, step 6; the title compound was prepared from the coupling of 3-bromo-4-(4-methylsulfonyl)phenyl-6-trifluoromethyl-pyran-2-one and 2-propanethiol.

$^1$H NMR (Acetone-d$_6$) δ 8.09 (d, 2H), 7.76 (d, 2H), 7.07 (s, 1H), 3.93 (m, 1H), 3.21 (s, 3H), 1.15 (d, 6H).

EXAMPLE 13

4-(4-Methylsulfonyl)phenyl-3-phenyl-6-(2,2,2-trifluoroethyl)-pyran-2-one

Step 1: To a solution of 4-(4-methylthio)phenyl-6-oxo-5-phenyl-6H-pyran-2-carbaldehyde, from example 5, step 1, (309 mg, 0.844 mmol) in cold (0° C.) THF (1.5 mL) was added CF$_3$SiMe$_3$ (142 mg, 1.01 mmol). TBAF (0.3 mL, 0.3 mmol) was then added and the mixture was stirred at 0° C. for 0.5 h and then warmed to r.t. for 2 h. HCl (6N) was added, and the mixture was extracted with EtOAc. The organic extracts were washed with brine, dried over anhyd. MgSO$_4$ and concentrated under vacuum. The residue was chromatographed on silica gel to give 276 mg (83%) of the corresponding trifluoromethanol intermediate.

Step 2: To a solution of the product of step 1 (126 mg, 0.32 mmol) in CH$_3$CN (0.5 mL) was added phenyl chlorothionoformate (60 mg, 0.35 mmol) and DMAP (51 mg, 0.41 mmol) at 0° C. The mixture was warmed to r.t. and stirred for 2 h, HCl (1N) was added and the mixture was extracted with EtOAc. The organic extracts were washed with brine, dried over anhyd. MgSO$_4$ and concentrated under vacuum. The residue was chromatographed on silica gel to give 157 mg (93%) of the corresponding thiocarbonate intermediate.

Step 3: To a solution of the product of step 2 (157 mg, 0.23 mmol) in toluene (1.5 mL) were added Bu$_3$SnCl (325 mg, 1 mmol), NaBH$_4$ (56 mg, 1.5 mmol) and AIBN (5 mg). The mixture was heated to reflux for 20 h. Chromatography of the mixture on silica gel gave 50 mg (58%) of the deoxygenated intermediate.

Step 4: To a solution of the product of step 3 (50 mg, 0.13 mmol) in CH$_2$Cl$_2$ was added mCPBA (52 mg, 0.3 mmol). The mixture was stirred at r.t. for 0.5 h. Aqueous NaHCO$_3$ was added and the mixture was extracted with EtOAc. The organic extracts were washed with brine, dried over anhyd. MgSO$_4$ and concentrated under vacuum. The residue was chromatographed on silica gel to give 24.8 mg (46%) of the title compound.

$^1$HNMR (Acetone-d$_6$) δ 7.85 (d, 2H), 7.47 (d, 2H), 7.23 (m, 5H), 6.70 (s, 1H), 3.74 (q, 2H), 3.09 (s, 3H).

EXAMPLE 14

3-(3-Hydroxy-3-methylbutyl)-6-methyl-4-(4-methylsulfonyl)phenyl-pyran-2-one

Step 1: 3-(3-hydroxy-3-methylbut-1-ynyl)-6-methyl-4-(4-methylthio)phenyl-pyran-2-one A mixture of 3-bromo-6-methyl-4-(4-methylthio)phenyl-pyran-2-one (1 g, 3.2 mmol), 2-methyl-3-butyn-2-ol (0.68 mL, 7.0 mmol), Et$_3$N (1.78 mL), dichlorobis(triphenylphosphine)palladium (0.45 g) and CuI (61 mg) in CH$_3$CN (32 mL) was degassed with 3 freeze/thaw cycles, then was refluxed for 3 hours. After cooling to r.t., EtOAc was added and the mixture was washed with water, brine (2×), dried over MgSO$_4$ and concentrated. The residue was purified by silica gel chromatography using 50% EtOAc/hexane, giving 569 mg of the title compound.

$^1$H NMR (Acetone-d$_6$) δ 7.65 (d, 2H), 7.37 (d, 2H), 6.40 (s, 1H), 4.46 (s, 1H), 2.56 (s, 3H), 2.30 (s, 3H), 1.45 (s, 6H).

Step 2: 3-(3-hydroxy-3-methylbut-1-ynyl)-6-methyl-4-(4-methylsulfonyl)phenyl-pyran-2-one A mixture of 3-(3-hydroxy-3-methylbut-1-ynyl)-6-methyl-4-(4-methylthio)phenyl-pyran-2-one (569 mg) and MMPP (1.34 g) was stirred in CH$_2$Cl$_2$ (23 mL) and MeOH (5.7 mL) for 2 h at r.t. Saturated sodium bicarbonate was added to the reaction mixture which was then extracted with CH$_2$Cl$_2$. The CH$_2$Cl$_2$ extract was washed with brine (2×), dried over MgSO$_4$ and concentrated. The residue was purified by silica gel chromatography and then swished in diethyl ether to give 496 mg of the title compound.

$^1$H NMR (Acetone-d$_6$) δ 8.08 (d, 2H), 7.98 (d, 2H), 6.45 (s, 1H), 4.48 (s, 1H), 3.18 (s, 3H), 2.33 (s, 3H), 1.40 (s, 6H).

Step 3: 3-(3-Hydroxy-3-methylbutyl)-6-methyl-4-(methylsulfonylphenyl)-pyran-2-one To a solution of 3-(3-hydroxy-3-methylbut-1-ynyl)-6-methyl-4-(4-methylsulfonyl)phenyl-pyran-2-one (50 mg) in EtOAc (1 mL) and EtOH (1 mL) was added 5% Pd/C (10 mg) and the mixture was hydrogenated under 30 psi for 1 hr. The mixture was then diluted with CH$_2$Cl$_2$, filtered on celite, and the solvent was evaporated under vacuum. Purification by silica gel chromatography using 80% EtOAc/hexane followed by trituration in ether afforded the title compound.

$^1$H NMR (Acetone-d$_6$) δ 8.06 (d, 2H), 7.68 (d, 2H), 6.12 (s, 1H), 3.18 (s, 3H), 2.44 (m, 2H), 2.26 (s, 3H), 1.64 (m, 2H), 1.07 (s, 6H).

The compounds of Formula I can be tested using the following assays to determine their cyclooxygenase-2 inhibiting activity.

Inhibition of Cyclooxygenase Activity

Whole cell assays for COX-2 and COX-1 using CHO transfected cell lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO[hCOX-1] and CHO[hCOX-2], respectively. For cyclooxygenase assays, CHO[hCOX-1] cells from suspension cultures and CHO[hCOX-2] cells prepared by trypsinization of adherent cultures are harvested by centrifugation (300×g, 10 min) and washed once in HBSS containing 15 mM HEPES, pH 7.4, and resuspended in HBSS, 15 mM HEPES, pH 7.4, at a cell concentration of 1.5×10$^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells (0.3×10$^6$ cells in 200 μl) are preincubated with 3 μl of the test drug or DMSO vehicle for 15 min at 37° C. Working solutions of peroxide-free AA (5.5 μM and 110 μM AA for the CHO[hCOX-1] and CHO[COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 μM AA in the CHO[hCOX-1] assay and a final concentration of 10 μM AA in the CHO[hCOX-2] assay. The reaction is terminated by the addition of 10 μl 1N HCl followed by neutralization with 20 μl of 0.5N NaOH. The samples are centrifuged at 300×g at 4° C. for 10 min, and an aliquot of the clarified supernatant is appropriately diluted for the determination of $PGE_2$ levels using an enzyme-linked immunoassay for $PGE_2$ (Correlate $PGE_2$ enzyme immunoassay kit, Assay Designs, Inc.). Cyclooxygenase activity in the absence of test compounds is determined as the difference in $PGE_2$ levels of cells challenged with arachidonic acid versus the $PGE_2$ levels in cells mock-challenged with ethanol vehicle. Inhibition of $PGE_2$ synthesis by test compounds is calculated as a percentage of the activity in the presence of drug versus the activity in the positive control samples.

Assay of COX-1 Activity from U937 cell microsomes

U937 cells are pelleted by centrifugation at 500×g for 5 min and washed once with phosphate-buffered saline and repelleted. Cells are resuspended in homogenization buffer consisting of 0.1M Tris-HCl, pH 7.4, 10 mM EDTA, 2 μg/ml leupeptin, 2 μg/ml soybean trypsin inhibitor, 2 μg/ml aprotinin and 1 mM phenyl methyl sulfonyl fluoride. The cell suspension is sonicated 4 times for 10 sec and is centrifuged at 10,000×g for 10 min at 4° C. The supernatant is centrifuged at 100,000×g for 1 hr at 4° C. The 100,000×g microsomal pellet is resuspended in 0.1M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 μg/ml in 0.1 M Tris-HCl buffer, pH 7.4 containing 10 mM EDTA, 0.5 mM phenol, 1 mM reduced glutathione and 1 μM hematin. Assays are performed in duplicate in a final volume of 250 μl. Initially, 5 μl of DMSO vehicle or drug in DMSO are added to 20 μl of 0.1M Tris-HCl buffer, pH 7.4 containing 10 mM EDTA in wells of a 96-deepwell polypropylene titre plate. 200 μl of the microsomal preparation are then added and pre-incubated for 15 min at room temperature before addition of 25 μl of 1M arachidonic acid in 0.1M Tris-HCl and 10 mM EDTA, pH 7.4. Samples are incubated for 40 min at room temperature and the reaction is stopped by the addition of 25 μl of 1N HCl. Samples are neutralized with 25 μl of 1N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

Assay of the activity of purified human COX-2

The enzyme activity is measured using a chromogenic assay based on the oxidation of N,N,N',N'-tetramethyl-p-phenylenediamine (TMPD) during the reduction of $PGG_2$ to $PGH_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 μL) contains 100 mM sodium phosphate, pH 6.5, 2 mM genapol X-100, 1 μM hematin, 1 mg/ml gelatin, 80–100 units of purified enzyme (One unit of enzyme is defined as the amount of enzyme required to produce an O.D. change of 0.001/min at 610 nm) and 4 μL of the test compound in DMSO. The mixture is pre-incubated at room temperature (22° C.) for 15 minutes prior to initiation of the enzymatic reaction by the addition of 20 μL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the % inhibition. $IC_{50}$ values are derived from 4-parameter least squares non-linear regression analysis of the log-dose vs % inhibition plot.

Human Whole Blood Assay

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2 mL blood aliquot to use as blank (basal levels of $PGE_2$). The remaining blood is incubated with LPS (100 μg/ml final concentration, Sigma Chem, #L-2630 from *E. coli*; diluted in 0.1% BSA (Phosphate buffered saline) for 5 minutes at room temperature. Five hundred μL aliquots of blood are incubated with either 2 μL of vehicle (DMSO) or 2 μL of a test compound at final concentrations varying from 10 nM to 30 μM for 24 hours at 37° C. At the end of the incubation, the blood is centrifuged at 12,000×g for 5 minutes to obtain plasma. A 100 μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000×g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

Rat Paw Edema Assay

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 ?l of 1% carrageenan solution in saline (FMC Corp, Maine) into the paw using an insulin syringe with a 25-gauge needle (i.e. 500 ?g carrageenan per paw). Three hr later, the paw volume ($V_3$) is measured and the increases in paw volume ($V_3$–$V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

LPS-Induced Pyrexia in Conscious Rats

Male Sprague-Dawley rats (150–200 g) were fasted for 16–18 h before use. At approximately 9:30 a.m., the animals were placed temporarily in plexiglass restrainers and their baseline rectal temperature was recorded using a flexible temperature probe (YSI series 400) connected to a digital thermometer (Model 08502, Cole Parmer). The same probe and thermometer were used for all animals to reduce experimental error. The animals were returned to their cages after the temperature measurements. At time zero, the rats were injected intraperitoneally with either saline or LPS (2 mg/kg, Sigma Chem) and the rectal temperature was remeasured at 5, 6 and 7 h following LPS injection. After the measurement at 5 h, when the increase in temperature had reached a plateau, the LPS-injected rats were given either the vehicle (1% methocel) or a test compound orally to determine whether the compound could reverse the pyrexia. Percent reversal of the pyrexia was calculated using the rectal temperature obtained at 7 h in the control (vehicle-treated) group as the reference (zero reversal) point. Complete reversal of pyrexia to the pre-LPS baseline value is taken as 100%.

LPS-Induced Pyrexia in Conscious Squirrel Monkeys

Temperature probes were surgically implanted under the abdominal skin in a group of squirrel monkeys (*Saimiri sciureus*) (1.0–1.7 kg). This allows for the monitoring of body temperature in conscious, unrestrained monkeys by a telemetric sensing system (Data Sciences International, Minnesota). The animals were fasted and were placed in individual cages for acclimatization 13–14 h before use. Electronic receivers were installed on the side of the cages which pick up signals from the implanted temperature probes. At approximately 9:00 a.m. on the day of the experiment, the monkeys were restrained temporarily in training chairs and were given a bolus I.V. injection of LPS, (6 mg/kg, dissolved in sterile saline). The animals were returned to their cages and body temperature was recorded continuously every 5 min. Two h after injection of LPS, when the body temperature had increased by 1.5–28 C, the monkeys were dosed orally with either vehicle (1% methocel) or a test compound (3 mg/kg). One hundred minutes later, the difference between the body temperature and the baseline value was determined. Percent inhibition was calculated taking the value in the control group as 0% inhibition.

Acute Inflammatory Hyperalgesia Induced by Carrageenan in Rats

Experiments were performed using male Sprague Dawley rats (90–110 g). Hyperalgesia to mechanical compression of the hind paw was induced by intraplantar injection of carrageenan (4.5 mg into one hind paw) 3 h previously. Control animals received an equivalent volume of saline (0.15 ml intraplantar). A test compound (0.3–30 mg/kg, suspended in 0.5% methocel in distilled water) or vehicle (0.5% methocel) was administered orally (2 ml/kg) 2 h after carrageenan. The vocalisation response to compression of the hind paw was measured 1 h later using a Ugo Basile algesiometer.

Statistical analysis for carrageenan-induced hyperalgesia was performed using one-way ANOVA (BMDP Statistical Software Inc.). Hyperalgesia was determined by subtracting the vocalisation threshold in saline injected rats from that obtained in animals injected with carrageenan. Hyperalgesia scores for drug-treated rats were expressed as a percentage of this response. $ID_{50}$ values (the dose producing 50% of the maximum observed response) were then calculated by non-linear least squares regression analysis of mean data using GraFit (Erithacus Software).

Adjuvant-Induced Arthritis in Rats

Seventy, 6.5–7.5 week old, female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 ml of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day-1) and 21 days following adjuvant injection, and primary paw volumes were determined before (day-1) and on days 4 and 21 following adjuvant injection. The rats were anesthetized with an intramuscular injection of 0.03–0.1 ml of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0. 1, 0.3, 1, and 3 mg/kg/day, Indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

Two-factor ('treatment' and 'time') analysis of variance with repeated measures on 'time' were applied to the % changes for body weight and foot volumes and to the rank-transformed radiographic total scores. A post hoc Dunnett's test was conducted to compare the effect of treatments to vehicle. A one-way analysis of variance was applied to the thymic and spleen weights followed by the Dunnett's test to compare the effect of treatments to vehicle. Dose-response curves for % inhibition in foot volumes on days 4, 14 and 21 were fitted by a 4-parameter logistic function using a non-linear least squares' regression. $ID_{50}$ was defined as the dose corresponding to a 50% reduction from the vehicle and was derived by interpolation from the fitted 4-parameter equation.

Pharmacokinetics in Rats

Per Os Pharmacokinetics in Rats

The animals are housed, fed and cared for according to the Guidelines of the Canadian Council on Animal Care. Male Sprague Dawley rats (325–375 g) are fasted overnight prior to each PO blood level study. The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed. Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.
Vehicles The following vehicles may be used in PO rat blood level determinations:

| |
|---|
| PEG 200/300/400: restricted to 2 mL/kg |
| Methocel 0.5%–1.0%: 10 mL/kg |
| Tween 80: 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \text{ (mg/kg)}}{AUCiv}$$

The units of CL are mL/h·kg (milliliters per hour kilogram)
Intravenous Pharmacokinetics in Rats The animals are housed, fed and cared for according to the Guidelines of the Canadian Council on Animal Care. Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles

The following vehicles may be used in IV rat blood level determinations:

| | |
|---|---|
| Dextrose: | 1 mL/kg |
| Moleculosol 25%: | 1 mL/kg |
| DMSO (dimethylsulfoxide): | Restricted to a dose volume of 0.1 mL per animal |
| PEG 200: | Not more than 60% mixed with 40% sterile water - 1mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \text{ (mg/kg)}}{AUCiv}$$

The units of CL are mL/h·kg (milliliters per hour kilogram)

NSAID-Induced Gastropathy in Rats

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 Ci) is injected per rat.

Protein-Losing Gastropathy in Squirrel Monkeys

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 Ci/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

The results for certain of the biological assays are shown in Table II.

TABLE II

| Example Number | Structure | COX-2 ($IC_{50}$ μM) | | COX-1 ($IC_{50}$ μM) | |
|---|---|---|---|---|---|
| | | CHO | HWB | U-937 | HWB |
| 1 | [structure with SO₂Me, pyranone, phenyl] | 0.12 | 2.6 | >10 | 13 |
| 2 | [structure with Me, SO₂Me, pyranone, 4-F-phenyl] | 0.4 | <0.4 | 0.3–1 | 2.0 |

TABLE II-continued

| Example Number | Structure | COX-2 (IC$_{50}$ μM) CHO | COX-2 (IC$_{50}$ μM) HWB | COX-1 (IC$_{50}$ μM) U-937 | COX-1 (IC$_{50}$ μM) HWB |
|---|---|---|---|---|---|
| 3 | Me-pyranone with 4-(4-SO$_2$Me-phenyl), 3-(3-F-phenyl) | 0.6 | <0.4 | 3–10 | 6.9 |
| 4 | Me-pyranone with 4-(4-SO$_2$Me-phenyl), 3-phenyl | 0.4 | <0.4 | 1 | 6.3 |
| 5 | CHF$_2$-pyranone with 4-(4-SO$_2$Me-phenyl), 3-phenyl | 0.2 | 1.8 | 0.3–1 | |
| 6 | CH$_2$F-pyranone with 4-(4-SO$_2$Me-phenyl), 3-phenyl | 1.1 | 3.1 | ~1 | |
| 7 | Me-pyranone with 4-(4-SO$_2$Me-phenyl), 3-SPh | 0.14 | 0.5 | 1–3 | 16 |
| 8 | Me-pyranone with 4-(4-SO$_2$Me-phenyl), 3-OPh | 0.2 | <0.4 | 1–3 | 13 |

TABLE II-continued

| Example Number | Structure | COX-2 (IC$_{50}$ μM) CHO | COX-2 (IC$_{50}$ μM) HWB | COX-1 (IC$_{50}$ μM) U-937 | COX-1 (IC$_{50}$ μM) HWB |
|---|---|---|---|---|---|
| 9 | | 2.9 | 0.6 | 0.3–1 | 16 |
| 10 | | 0.8 | 1.3 | >10 | |
| 11 | | 0.01 | 0.3–1 | 14 | |
| 12 | | 0.06 | 1–3 | >33 | |
| 13 | | 0.37 | 10.5 | 10 | |
| 14 | | 2.8 | 1.2 | >10 | |

What is claimed is:

1. A compound of Formula I:

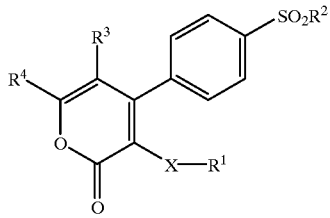

I or a pharmaceutically acceptable salt thereof wherein:
X is selected from the group consisting of:
(a) a bond,
(b) —(CH$_2$)$_m$—, wherein m 1 or 2,
(c) —C(O)—,
(d) —O—,
(e) —S—, and
(f) —N(R$^5$)—;
R$^1$ is selected from the group consisting of:
(a) C$_{1-10}$alkyl, optionally substituted with 1–3 substituents independently selected from the group consisting of:
(1) hydroxy,
(2) halo,
(3) C$_{1-10}$alkoxy,
(4) C$_{1-10}$alkylthio, and
(5) CN,
(b) phenyl or naphthyl, and
(c) heteroaryl, which is comprised of a monocyclic aromatic ring of 5 atoms having one hetero atom which is S, O or N, and optionally 1, 2, or 3 additional N atoms; or
a monocyclic ring of 6 atoms having one hetero atom which is N, and optionally 1, 2, or 3 additional N atoms,
wherein groups (b) and (c) above are each optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and
(6) N$_3$;
R$^2$ is selected from the group consisting of
(a) C$_{1-6}$alkyl, optionally substituted to its maximum with halo,
(b) NH$_2$, and
(c) NHC(O)C$_{1-10}$alkyl, optionally substituted to its maximum with halo;
R$^3$ and R$^4$ are each independently selected from the group consisting of:
(a) hydrogen,
(b) halo, and
(c) C$_{1-6}$alkyl, optionally substituted to its maximum with halo; and
R$^5$ is selected from the group consisting of:
(a) hydrogen and
(b) C$_{1-6}$alkyl, optionally substituted to its maximum with halo.

2. A compound according to claim 1 wherein X is a bond.
3. A compound according to claim 1 wherein X is —O—.
4. A compound according to claim 1 wherein X is —S—.
5. A compound according to claim 1 wherein R$^2$ is CH$_3$.
6. A compound according to claim 1 wherein R$^3$ is hydrogen.
7. A compound according to claim 1 wherein m is 1.
8. A compound according to claim 1 wherein R$^1$ is phenyl, optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and
(6) N$_3$.
9. A compound according to claim 8 wherein R$^2$ is CH$_3$.
10. A compound according to claim 8 wherein R$^3$ is H.
11. A compound according to claim 1 wherein R$^1$ is heteroaryl, which is comprised of a monocyclic aromatic ring of 5 atoms having one hetero atom which is S, O or N, and optionally 1, 2, or 3 additional N atoms; or a monocyclic ring of 6 atoms having one hetero atom which is N, and optionally 1, 2, or 3 additional N atoms, wherein heteroaryl is optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and
(6) N$_3$.
12. A compound according to claim 11 wherein R$^1$ is pyridyl, optionally substituted with 1–3 substituents independently selected from the group consisting of:
(1) halo,
(2) C$_{1-10}$alkoxy,
(3) C$_{1-10}$alkylthio,
(4) CN,
(5) C$_{1-10}$alkyl, optionally substituted to its maximum with halo, and (6) N$_3$.
13. A compound according to claim 1 wherein R$^1$ is C$_{1-6}$alkyl, optionally substituted with hydroxy.
14. A compound selected from the group consisting of:
(a) 4-(4-Methylsulfonyl)phenyl-3-phenyl-pyran-2-one,
(b) 3-(4-Fluorophenyl)-6-methyl-4-(4-methylsulfonyl)phenyl-pyran-2-one,
(c) 3-(3-Fluorophenyl)-6-methyl-4-(4-methylsulfonyl)phenyl-pyran-2-one,
(d) 6-Methyl-4-(4-methylsulfonyl)phenyl-3-phenyl-pyran-2-one,
(e) 6-Difluoromethyl-4-(4-methylsulfonyl)phenyl-3-phenyl-pyran-2-one,
(f) 6-Fluoromethyl-4-(4-methylsulfonyl)phenyl-3-phenyl-pyran-2-one,
(g) 6-Methyl-4-(4-methylsulfonyl)phenyl-3-phenylthio-pyran-2-one,
(h) 6-Methyl-4-(4-methylsulfonyl)phenyl-3-phenoxy-pyran-2-one,
(i) 6-Methyl-4-(4-methylsulfonyl)phenyl-3-pyridin-3-yl-pyran-2-one, (j) 3-Isopropylthio-6-methyl-4-(4-methylsulfonyl)phenyl-pyran-2-one,
(k) 4-(4-Methylsulfonyl)phenyl)-3-phenylthio-6-trifluoromethyl-pyran-2-one,
(l) 3-Isopropylthio-4-(4-methylsulfonyl)phenyl-6-trifluoromethyl-pyran-2-one,
(m) 4-(4-Methylsulfonyl)phenyl-3-phenyl-6-(2,2,2-trifluoroethyl)-pyran-2-one, and
(n) 3-(3-Hydroxy-3-methylbutyl)-6-methyl-4-(4-methylsulfonyl)phenyl-pyran-2-one.

15. A pharmaceutical composition comprising a compound according to claim 1 in combination with a pharmaceutically acceptable carrier.

16. A method of treating or preventing an inflammatory disease in a mammalian patient in need of such treatment or prevention comprising administering to said patient a compound according to claim 1 in an amount effective to treat or prevent said inflammatory disease.

17. A method of treating or preventing a cyclooxygenase-2 mediated disease advantageously treated by an active agent that selectively inhibits cyclooxygenase-2 in preference to cyclooxygenase-1 in a mammalian patient in need of such treatment or prevention comprising administering to said patient a compound according to claim 1 in an amount effective to treat or prevent said cyclooxygenase-2 mediated disease.

18. The compound according to claim 1 used in the manufacture of a medicament for the treatment of an inflammatory disease susceptible to treatment with a non-steroidal anti-inflammatory agent.

* * * * *